(12) United States Patent
Haywood et al.

(10) Patent No.: US 6,899,850 B2
(45) Date of Patent: May 31, 2005

(54) METHOD AND BASKET APPARATUS FOR TRANSPORTING BIOLOGICAL SAMPLES

(75) Inventors: Bruce C. Haywood, Franklin Lakes, NJ (US); Jamieson W. M. Crawford, New York, NY (US); Bradley M. Wilkinson, No. Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 61 days.

(21) Appl. No.: 10/269,035

(22) Filed: Oct. 11, 2002

(65) Prior Publication Data

US 2003/0087423 A1 May 8, 2003

Related U.S. Application Data

(60) Provisional application No. 60/328,397, filed on Oct. 12, 2001.

(51) Int. Cl.[7] .................................................. B01L 3/02
(52) U.S. Cl. .................... 422/102; 422/99; 422/101; 435/288.1; 435/288.2; 215/306; 220/23.83; 220/23.87; 220/23.89
(58) Field of Search ............................ 422/58, 99, 101, 422/102; 436/174, 176, 177, 178; 435/283.1, 288.1, 288.2; 220/23.83, 23.87, 23.89, 23.9; 215/306

(56) References Cited

U.S. PATENT DOCUMENTS

| | | | |
|---|---|---|---|
| 2,302,698 A | 11/1942 | Kessel | |
| 4,009,777 A | 3/1977 | Thomas | |
| 4,205,747 A | 6/1980 | Gilliam et al. | |
| 4,257,521 A | 3/1981 | Poler et al. | |
| 4,277,172 A | 7/1981 | Richards | |
| 4,326,306 A | 4/1982 | Poler | |
| 4,423,809 A | 1/1984 | Mazzocco | |
| 4,439,319 A | 3/1984 | Rock | |
| 4,697,697 A | 10/1987 | Graham et al. | |
| 4,721,124 A | * 1/1988 | Tuerkheimer et al. | 134/138 |
| 4,750,610 A | 6/1988 | Ryder et al. | |
| 4,801,553 A | 1/1989 | Owen et al. | |
| 4,844,242 A | 7/1989 | Chen et al. | |
| 5,061,452 A | * 10/1991 | Yamamoto et al. | 422/101 |
| 5,101,967 A | * 4/1992 | Sibley | 206/5.1 |
| 5,143,104 A | * 9/1992 | Iba et al. | 134/135 |
| 5,181,604 A | * 1/1993 | Ohta et al. | 206/5.1 |
| 5,269,671 A | * 12/1993 | McCormick | 425/117 |
| 5,281,227 A | 1/1994 | Sussman | |
| 5,424,040 A | 6/1995 | Bjornsson | |
| 5,427,742 A | * 6/1995 | Holland | 422/102 |
| 5,518,612 A | 5/1996 | Kayal et al. | |
| 5,533,642 A | * 7/1996 | Lafond et al. | 220/326 |
| 5,543,114 A | * 8/1996 | Dudek | 422/102 |
| 5,558,846 A | * 9/1996 | Alvord et al. | 422/301 |
| 5,609,827 A | 3/1997 | Russell et al. | |
| 5,665,398 A | * 9/1997 | McCormick | 425/117 |
| 5,681,740 A | * 10/1997 | Messier et al. | 435/284.1 |
| 5,817,032 A | 10/1998 | Williamson, IV et al. | |
| 5,928,935 A | 7/1999 | Reuss, Jr. et al. | |
| 5,941,260 A | * 8/1999 | Wershe | 134/117 |
| 6,017,476 A | * 1/2000 | Renshaw | 264/158 |
| 6,204,375 B1 | 3/2001 | Lader | |
| 6,248,535 B1 | 6/2001 | Danenberg et al. | |
| 6,375,028 B1 | * 4/2002 | Smith | 220/258.1 |
| 6,513,673 B2 | * 2/2003 | Alley | 220/524 |
| 2001/0017271 A1 | 8/2001 | Yavitz | |

* cited by examiner

*Primary Examiner*—Jill Warden
*Assistant Examiner*—Dwayne K Handy

(57) ABSTRACT

A container assembly for storing and stabilizing a biological sample includes a container, a closure cap and a sample holder coupled to the closure cap and removably received in the container. The sample holder can be a basket-like device coupled to an inner face of the cap and includes a central cavity for receiving the sample and immersing the sample in the reagent in the container. The closure cap includes a body member with a dimension to displace a volume of air and reduce the head space to ensure that the sample holder is completely immersed in the reagent. The sample holder has a closure member for closing the open top end of the cavity.

42 Claims, 11 Drawing Sheets

METHOD AND BASKET APPARATUS FOR TRANSPORTING BIOLOGICAL SAMPLES

This application claims the benefit under 35 U.S.C. § 119(e) of Provisional Application No. 60/328,397, filed Oct. 12, 2001, which is hereby incorporated by reference in its entirety.

FIELD OF THE INVENTION

The present invention is directed to a method and apparatus for collecting, transporting, processing and storing biological samples, such as tissue samples, in a reagent. The invention is also directed to a method and basket apparatus for collecting, transporting and storing small biological samples in a sample holder that is coupled to the closure cap of a container to completely immerse the sample in a reagent.

BACKGROUND OF THE INVENTION

Biological samples are often obtained by researchers and clinicians in the field of histopathology. Samples are collected for diagnostic evaluation to determine the presence of a certain disease and to determine an appropriate treatment for the disease. Common diagnostic processes for diseases include histological and cytological diagnosis. For example, tumors are typically examined for histological and cytological abnormalities.

Biological samples are also obtained for molecular diagnostic evaluation. In recent years, nucleic acid analysis and studies have become common place in research for the treatment of numerous diseases. An essential requirement for accurate nucleic acid qualitative and quantitative analysis is the presence of high quality and intact nucleic acids. For example, intact nucleic acid is necessary for RT-PCR, Northern blot hybridization and nuclease protection assays analysis of nucleic acid expressions.

Biological samples can be obtained from various sources and by various processes. Numerous devices exist that are designed to remove a small amount of sample from an organ or other specimen. For example, small samples can be obtained by surgical processes such as by use of a scalpel or a device similar to a punch to extract core fragments of tissue. Another device for performing a biopsy uses a needle device that can extract single cells, small cell clumps and tissue fragments.

Generally, it is preferable to prepare a biological sample for subsequent analysis immediately after being extracted from the patient or source to obtain the most accurate results possible. Numerous molecular, cellular and morphological changes can occur in the sample during collection and transport, which can affect the final results. For example, nucleic acid in a biological sample can undergo numerous changes, such as up regulation, down regulation and degradation. The rate of these changes can be affected by temperature.

The analysis of a biological sample at the time of collection is often impossible or not practical. Therefore, it is necessary to store the sample under controlled conditions to prevent or inhibit degradation of the sample and to retain the integrity of the results of the analysis. Biological samples are typically stored in a container with a suitable fixative reagent. A typical fixative reagent is 10% formalin. Other fixatives include water miscible alcohols, ethanol/acetone mixtures, and ethanol/acetic acid mixtures. Ammonium sulfate solutions have also been used as disclosed in U.S. Pat. No. 6,204,375 to Lader, which is hereby incorporated by reference in its entirety. The containers with the biological sample in the fixative reagent can then be sent to a pathology laboratory or other destination for analysis.

Proper handling of the biological sample is essential for accurate analysis, and particularly for nucleic acid quantitative and qualitative evaluation. The biological samples require an effective amount of the fixative reagent to preserve the sample. In addition, some reagents are required to completely cover the sample with the reagent to ensure effective preservation. Typically, the biological samples are simply placed in a small container for storage. The biological samples which can be very small can be difficult to locate and recover from the container.

To obtain high quality test results, early stabilization of specimens may be required. For example, biological samples can be quick frozen by various methods, such as with liquid nitrogen or dry ice, as known in the art. The samples are usually preserved in formaldehyde and alcohol based solutions and chaotropic salt.

Quick freezing of biological samples can be effective in stabilizing cellular and molecular characteristics. Quick freezing is not always convenient or available. Typically, the collection location and processing laboratory are separated in location and time, which create an impediment to stabilization.

The prior methods for collecting, storing, transporting and stabilizing biological samples have known limitations. Accordingly, there is a continuing need in the industry for an improved method and container for collecting, transporting, storing and processing biological samples.

SUMMARY OF THE INVENTION

The present invention is directed to a method and sample holder apparatus for collecting, transporting, processing and storing biological samples in a liquid reagent. The invention is also directed to a method and sample holder apparatus for maintaining a biological sample completely immersed in a reagent.

Accordingly, a primary aspect of the invention is to provide a method and container apparatus for collecting, transporting, storing and processing a biological sample in a reagent. The method is particularly suitable for treating whole tissue samples and cells.

Another aspect of the invention is to provide a method for harvesting, transporting and storing a biological sample in a reagent where the sample can be easily recovered from the reagent.

Still another aspect of the invention is to provide a method and apparatus for collecting, storing, stabilizing, processing and/or transporting a biological sample in a reagent and regulating the relative amount of the biological sample to the amount of the surrounding reagent based on the weight, volume and density of the biological sample.

Another aspect of the invention is to provide an assembly having a container for a treating reagent and a removable sample holder for receiving and retaining a biological sample completely immersed in the reagent without regard for the orientation of the container.

A further aspect of the invention is to provide a method and apparatus for defining a containment area for a biological sample where the containment area is oriented in a container to remain immersed in a reagent within the container.

Another aspect of the invention is to provide a container and sample holder that is able to accommodate different size biological samples and to contain a controlled amount of a reagent for the sample size to treat the sample effectively.

Another aspect of the invention is to provide a kit or packaged assembly of components for harvesting, transporting, storing and treating a biological sample. The kit includes a sample holder having a cavity to receive the biological sample and a container with the treating reagent and having a dimension to receive the sample holder. The kit also includes tools for obtaining the tissue sample such as a scalpel, forceps, measuring gauge, and the like. Preferably, the kit is packaged in a clean and sterile environment.

Another aspect of the invention is to provide a container assembly for stabilizing a biological sample in a nucleic acid stabilizing agent for extended periods of time and for obtaining intact nucleic acid from the sample for nucleic acid isolation and molecular diagnostic evaluation.

Still another aspect of the invention is to provide a container assembly for storing a biological sample and immersing the biological sample in a reagent, wherein the container assembly is prefilled with the reagent.

A further aspect of the invention is to provide a container assembly for treating a biological sample with a reagent, where the assembly includes a biological sample holder coupled to a cap of a container and having a chamber for receiving the sample of a predetermined size to limit the size of the biological sample in relation to the volume of the reagent in the container.

Still another aspect of the invention is to provide a biological sample container assembly for contacting a biological sample with a reagent where the assembly has a sample holder coupled to a closure cap of the container to limit spilling of the reagent when the sample holder is removed from a container.

A further aspect of the invention is to provide a container assembly for receiving a biological sample where the assembly includes a container and a removable sample holder coupled to a cap of the container, where the sample holder has an open end that is closed by a closure member.

Another aspect of the invention is to provide a biological sample container assembly including a reagent container and a sample holder coupled to a closure cap of the container, where the sample holder has a dimension to displace an amount of air and a reagent in the container to immerse the sample holder completely in the reagent in the container.

A further aspect of the invention is to provide a biological sample container assembly including a container, a cap and a sample holder coupled to the cap, where the sample holder has at least one connecting member for spacing the sample holder from the cap to position the sample holder in a selected location within the container.

Another aspect of the invention is to provide a container assembly for a biological sample including a container and sample holder having a cavity enclosed by permeable surfaces to enable the free flow of a reagent around the biological sample within the cavity. The permeable surfaces are made of liquid permeable media, such as a mesh material, filter paper or porous membrane screen.

A still further aspect of the invention is to provide a biological sample container assembly including a container, a closure cap and a sample holder coupled to the cap, where the sample holder includes a base that mates with a recess in the cap.

In one embodiment of the invention, the container assembly includes a container, a closure cap, and sample holder coupled to the cap and dimensioned to fit within the container. The sample holder is a basket-like device having an outer wall and an open end. The sample holder includes a recessed area for supporting a biological sample. The recessed area is formed by a porous section of the outer wall to allow the free flow of a liquid reagent through the recessed area and around the biological sample. The closure member is coupled to the sample holder to close the open end. The closure member can be pivotally connected to the sample holder.

In another embodiment, the sample holder has a substantially spherical shape with a first semi-spherical shape member and a second semi-spherical shaped member. The first member includes a post coupled to a cap of a container. The second semi-spherical shaped member is pivotally connected to the first member and includes a handle for operating the second member.

These and other aspects of the invention are basically attained by providing a container assembly for storing a biological sample. The container has a bottom, a side and an open top end. The container also has a dimension to contain a volume of a reagent sufficient to treat a biological sample. A cap is provided for coupling to the open top end of the container. A sample holder is coupled to the cap and is to be positioned in a selected location in the container. The sample holder has an internal cavity with a dimension for receiving a biological sample and has a plurality of fluid openings into the cavity to enable free flow of the reagent to the biological sample contained therein. The sample holder also has a dimension to fit between the bottom and side of the container and the cap and to immerse the cavity in the reagent.

The aspects of the invention are further attained by providing a container assembly comprising a container having a bottom, a side and an open top end, and being dimensioned to contain a treating liquid. A cap having an outer face and an inner face is removably coupled to the container and closes the open top end of the container. A sample holder is coupled to the inner face of the lid and has an internal cavity for receiving a biological sample. The sample holder has at least one fluid opening into the cavity and has a dimension to fit within the container to completely immerse the cavity in the tissue treating liquid. The sample holder is positioned on the inner face of the cap to substantially prevent linear movement of the sample holder in the container. A body extends from the inner face of the cap to displace a portion of air and the treating liquid in the container to raise the level of the liquid reagent to maintain the cavity of the sample holder immersed in the liquid reagent.

The aspects of the invention are still further attained by providing a method of stabilizing nucleic acids in cells and biological samples comprising the steps of providing a container having a bottom, a side and an open top end. The container contains a tissue treating liquid including a nucleic acid stabilizing agent. A biological sample is placed in a sample holder which has an internal cavity for receiving the biological sample and a fluid opening into the cavity. The sample holder is coupled to an inner face of the cap of the container to completely immerse the cavity in the treating liquid.

The various aspects, advantages and other salient features of the invention will become apparent from the annexed drawings and the following detailed description of the invention.

BRIEF DESCRIPTION OF THE DRAWINGS

The following is a brief description of the drawings, in which.

DETAILED DESCRIPTION OF THE INVENTION

Figure 1:
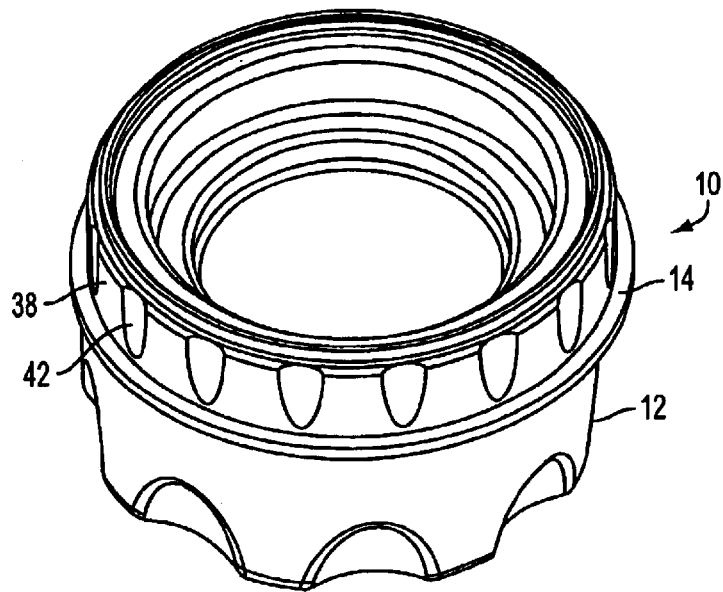
FIG. 1 is a perspective view of the container assembly in a first embodiment.

The present invention is directed to a method and apparatus for collecting, storing, stabilizing, processing and transporting biological samples. The invention is directed to a method and apparatus for transporting biological samples in a reagent, such as a liquid stabilizing agent.

The method and apparatus of the invention are particularly suitable for transporting biological samples for various processes, such as for molecular diagnostic processes. The biological samples are stored in a container assembly that contains a liquid reagent so that the biological sample is completely immersed in the reagent during storage and transport. The reagent can be, for example, an agent that is able to preserve nucleic acids in the cells of tissues for extended periods of time. The sample can then be transported to a suitable laboratory and processed to extract intact nucleic acids, such as RNA for quantitative and qualitative analysis.

The invention is particularly directed to a method of storing a biological sample in a container and treating the biological sample with an effective amount of a treating reagent. The method ensures that the sample contacts an amount of the reagent that is effective to treat the sample and to maintain the sample immersed in the reagent to prevent or minimize contact of the sample with air. In one embodiment, the container is filled to a predetermined level with a liquid reagent so that when the sample and sample holder are placed in the container, the level of the liquid reagent rises to ensure the sample is submerged in the liquid reagent. Preferably, the sample holder retains the sample in a predetermined containment area of the container to retain the sample immersed in the reagent regardless of the orientation of the container. In other embodiments the reagent can be a solid or semi-solid. Typically the solid or semi-solid reagents are in the form of beads or particles.

The method and container assembly of the invention provide for the control and regulation of the relative amounts of the biological sample and the reagent to ensure complete and efficient treatment of the sample. The container assembly enables the operator to control the size of the biological sample in relation to the volume of the stabilizing liquid available in the container to maintain effective treatment of the sample. In preferred embodiments, the biological sample is maintained completely submerged in the reagent within the container regardless of the orientation of the container. By retaining the biological sample in a selected containment area of a storage container, the sample is immersed in the treating reagent during storage and transport.

Referring to FIGS. 1–10, a first embodiment of the invention is shown directed to a container assembly 10. Container assembly 10 includes a container 12, a lid or closure cap 14 and a sample holder 16.

In the embodiment illustrated, container 12 has a substantially cylindrical shape formed by a side wall 18 and a bottom wall 20. Side wall 18 extends between an open top end 22 of container 12 and a bottom edge 24. A plurality of recessed areas 26 are formed in side wall 18 adjacent bottom edge 24. Recesses 26 have a dimension to assist the operator in gripping the container 12 when opening and closing container assembly 10.

Side wall 18 includes external threads 28 adjacent open top end 22 for mating with complementing threads on cap 14. A rib 30 extends radially outward from side wall 18 and is spaced axially from open top end 22. Rib 30 preferably is spaced from open top end 22 a distance complementing the dimensions of closure cap 14 and encircles container 12.

Figure 10:
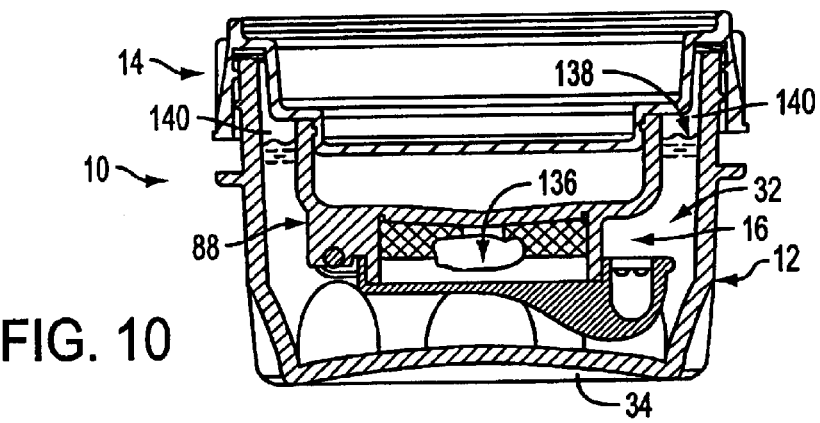
FIG. 10 is a cross-sectional side view of the sample holder and cap on the container.

Referring to FIG. 10, container 12 has an internal cavity 32 with a dimension sufficient to contain an effective amount of a liquid reagent sufficient to treat a biological sample. In the embodiment illustrated, bottom wall 20 has a dome shape extending from bottom edge 24 of side wall 18 to form a concave recess 34 in the bottom of container 12. In alternative embodiments, the bottom of container 12 can be substantially flat.

Figure 2:
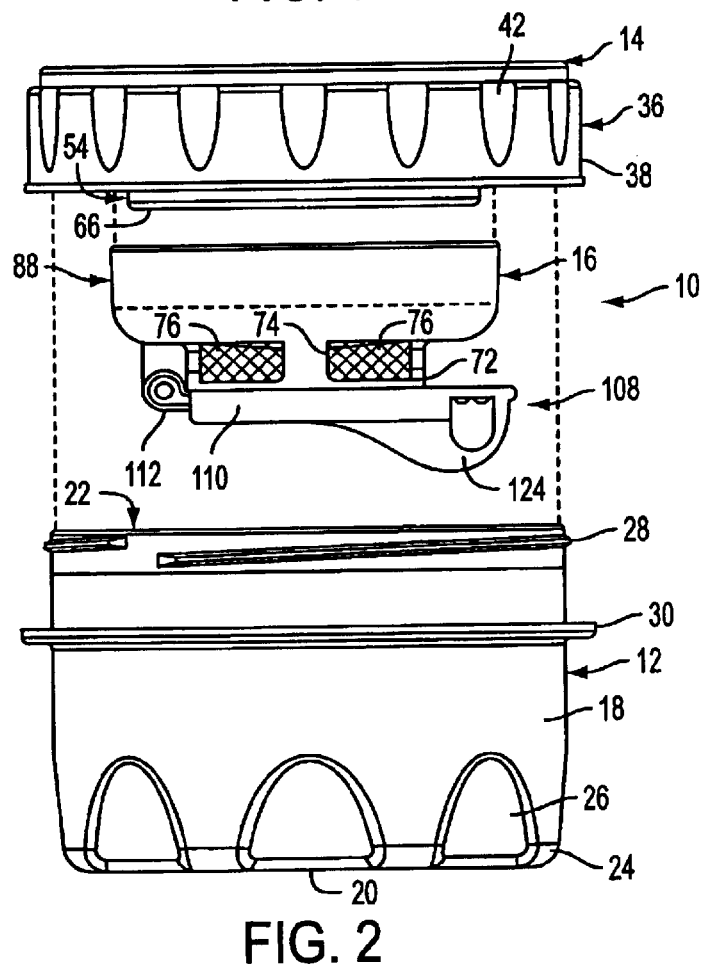
FIG. 2 is an exploded side view of the container assembly showing the cap, sample holder, and the container.
Figure 4:
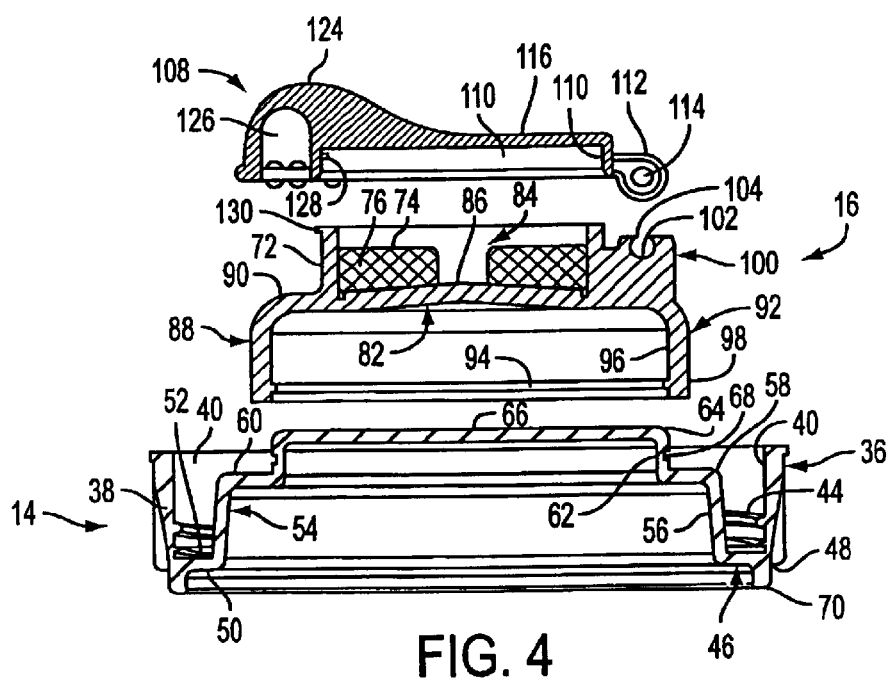
FIG. 4 is an exploded cross-sectional side view of the sample holder and cap.
Figure 5:
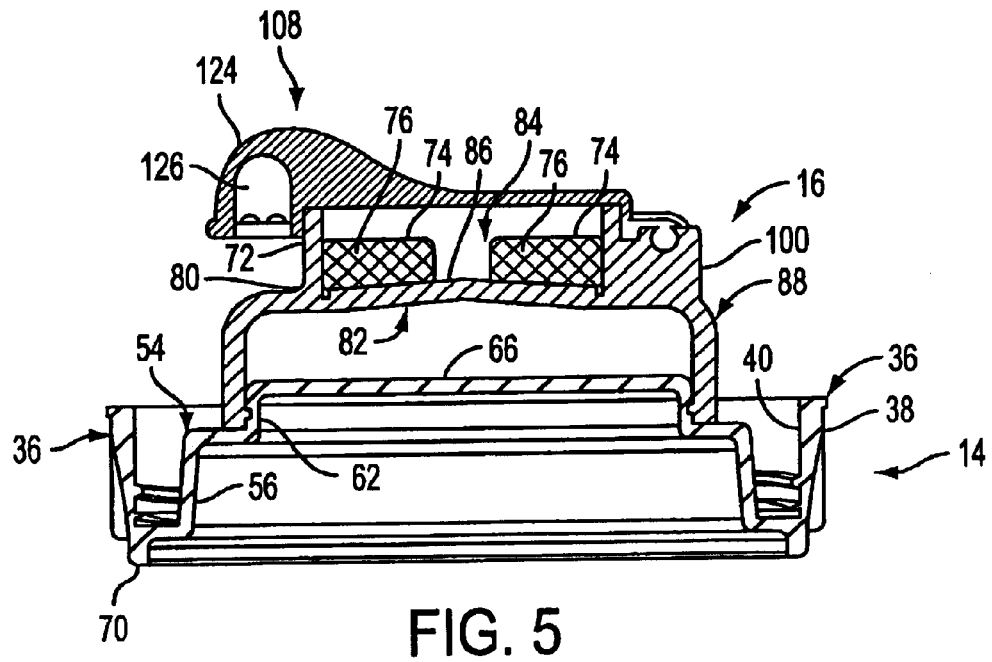
FIG. 5 is a cross-sectional view of the assembled sample holder and cap.
Figure 6:
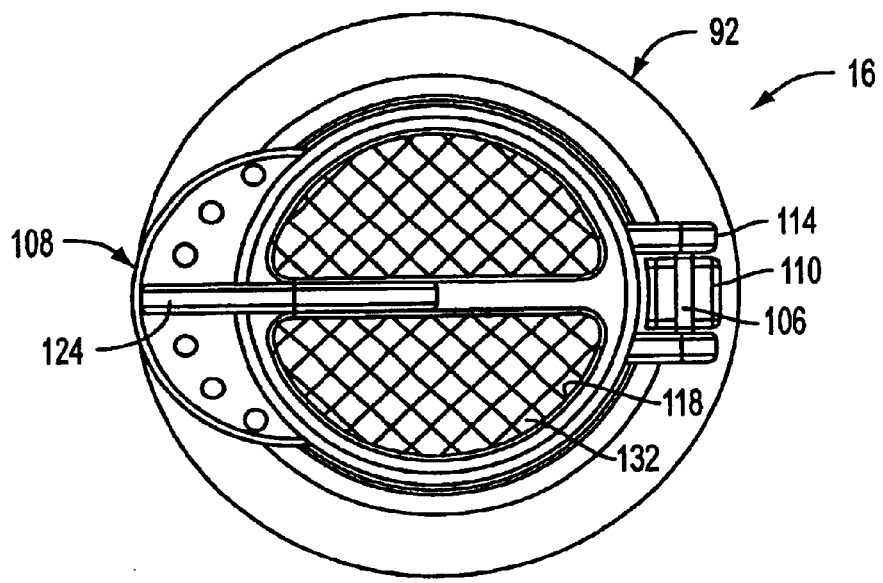
FIG. 6 is a top view of the sample holder.

Cap 14 has a dimension complementing side wall 18 of container 12 for mating with container 12. As shown in FIGS. 2, 4 and 10, cap 14 includes a side wall 36 having a substantially cylindrical shape with an outer surface 38 and an inner surface 40. As shown in FIG. 2, outer surface 38 includes a plurality of dimples 42 to assist the operator in handling cap 14. Inner surface 40 includes threads 44 for mating with threads 28 of container 12.

As shown in FIG. 4, closure cap 14 has a top wall 46 coupled to a top end 48 of side wall 36. Top wall 46 has a top surface 50 and a bottom surface 52. A body portion 54 extends from top wall 46 in a substantially axial direction from bottom surface 52 toward a bottom end of side wall 36. Body portion 54 has a substantially cylindrical shaped annular side wall 56 extending in an axial direction from top wall 46. Side wall 56 has an outer end 58 having a shoulder 60 extending radially inward with respect to cap 14. Shoulder 60 is coupled to an annular wall 62 which extends in an axial direction from shoulder 60 and is concentric with side wall 56. Annular wall 62 has an outer end 64 that is coupled to an end wall 66. Annular wall 62 in the embodiment illustrated has a recess 68 extending around the circumference of wall 62 for coupling with sample holder 16. In preferred embodiments, an annular rib 70 extends in an axial direction from top end 48 of side wall 36. Annular rib 70 extends from top surface 50 of cap 14 to form a ledge with top wall 46 that has an inner dimension to complement bottom edge 24 of side wall 18 of container 12. Container assemblies 10 can be stacked vertically with bottom edge 24 of a respective container 12 received in the area defined by annular rib 70.

Sample holder 16 includes a side wall 72 having a plurality of openings 74. Openings 74 are covered by a liquid permeable material 76 such as a nylon mesh. Alternatively, the permeable material can be filter paper or a porous membrane screen. Generally, permeable material 76 is applied to the inner or outer surface of side wall 72 by a suitable adhesive. In other embodiments, side wall 72 can be formed with porous surfaces that allow the treating liquid to flow through the cavity while retaining a biological sample in the vessel. Side wall 72 has a substantially cylindrical shape with an open top end 78 and a bottom end 80. A bottom wall 82 is coupled to side wall 72 at bottom end 80 to define an internal cavity 84 having a closed bottom. As shown in FIG. 4, bottom wall 82 has a substantially frustoconical shape forming a raised center portion 86.

Sample holder 16 includes a base 88 coupled to bottom end 80 of side wall 72. Base 88 has a top wall 90 and a side wall 92 extending in a substantially axial direction with respect to sample holder 16. Side wall 92 has a substantially cylindrical shape complementing the dimension of annular wall 62 of cap 14. Side wall 92 includes a rib 94 extending radially inward from an inner surface 96 of side wall 92 adjacent an outer end 98. Rib 94 has a dimension complementing recess 68 for coupling sample holder 16 to cap 14. In the embodiment illustrated, sample holder 16 is coupled to closure cap 14 by an interference fit. In alternative embodiments, sample holder 16 can be coupled to closure cap 14 by a friction fit, adhesive or other suitable fastener. Sample holder 16 can also be integrally molded with cap 14.

Figure 3:
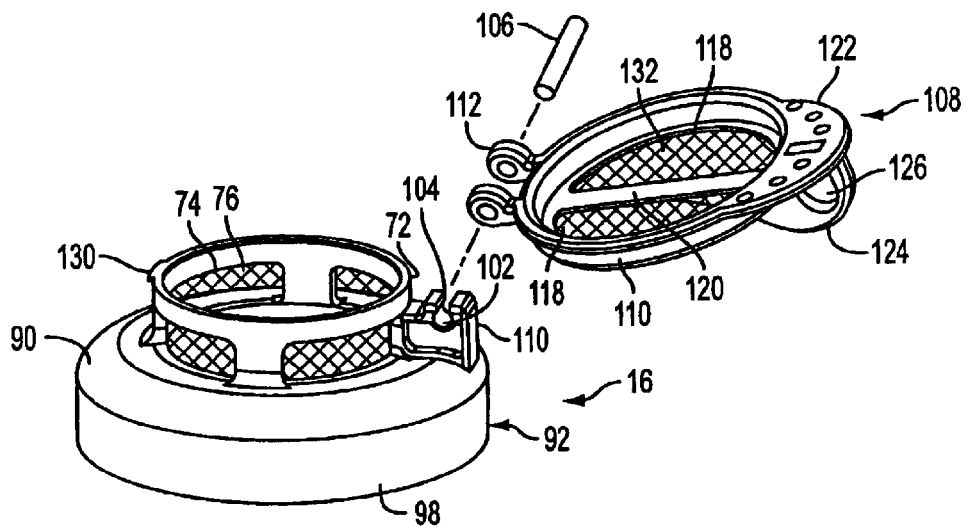
FIG. 3 is an exploded perspective view of the sample holder of FIG. 2.

A hinge 100 is provided on top wall 90 of base 88 and side wall 72 as shown in FIG. 4. Hinge 100 includes an arcuate shaped recess 102 with an open end 104 for receiving a hinge pin 106 as shown in FIG. 3. A closure 108 includes a side wall 110 having a circular shape with an inner dimension complementing the outer dimension of side wall 72 of sample holder 16. A hinge 112 having an aperture 114 is coupled to an outer surface of side wall 108. Aperture 114 has a dimension to receive hinge pin 106 for coupling closure 108 to hinge 100. In this embodiment, closure 108 pivots about an axis substantially perpendicular to an axis of side wall 110.

Closure 108 includes a top wall 116 coupled to side wall 110. In the embodiment illustrated, top wall 116 includes a two semi-circular openings 118 forming a center rib 120. A lip 122 extends radially outward from side wall 110 opposite from hinge 112. A handle 124 is coupled to lip 122 and center rib 120 to assist in opening and closing closure 108. Handle 124 in the embodiment illustrated includes an aperture 126 to assist in gripping handle 124. Side wall 110 of closure 108 includes a detent 126 for mating with a detent 130 on side wall 72 for retaining closure 108 in a closed position. As shown in FIGS. 5–9, closure 108 is pivotally coupled to side wall 72 and can be pivoted between an open position shown in FIG. 8 and a closed position shown in FIGS. 5 and 7. In other embodiments, closure 108 is coupled to sample holder 16 by a living hinge or can be a separate member that can be completely separated from sample holder 16.

Cavity 84 of sample holder 16 has a dimension sufficient to contain a suitable size of a biological sample for analysis. Cavity 84 is defined by side wall 72 and closure 108 and has sufficient openings to allow the free flow of the reagent through cavity 84. Openings 118 in top wall 116 of closure 108 include a permeable material 132 such as a mesh material. The permeable mesh material preferably has a pore size sufficient to allow liquid to pass through cavity 84 while retaining a biological sample within cavity 84.

Container assembly 10 is preferably made of a molded plastic material that is non-reactive with the reagents and does not interfere with the analysis of the biological sample being transported therein. Closure cap 14 is preferably molded as a one piece integrally formed member. Sample holder 16 is also preferably molded as a one piece unit. In the embodiment illustrated, sample holder 16 is a separate component from closure cap 14 that is snapped together. In alternative embodiments, sample holder 16 can be integrally formed with closure cap 14 or coupled to closure cap 14 by an adhesive or other fastener.

In a preferred embodiment, container assembly 10 is manufactured and sold as an assembled unit and is prefilled with a liquid reagent. Container assembly 10 is sealed, packaged and shipped to the physician for storing a biological sample for analysis at a later time. Container assembly 10 can include a suitable seal or tamper indicator as known in the art. In alternative embodiments, container assembly 10 can be packaged without a reagent and shipped to the physician empty. Cap 14 can be removed from container 12 and filled with a suitable reagent at the time of use by the physician.

Figure 7:
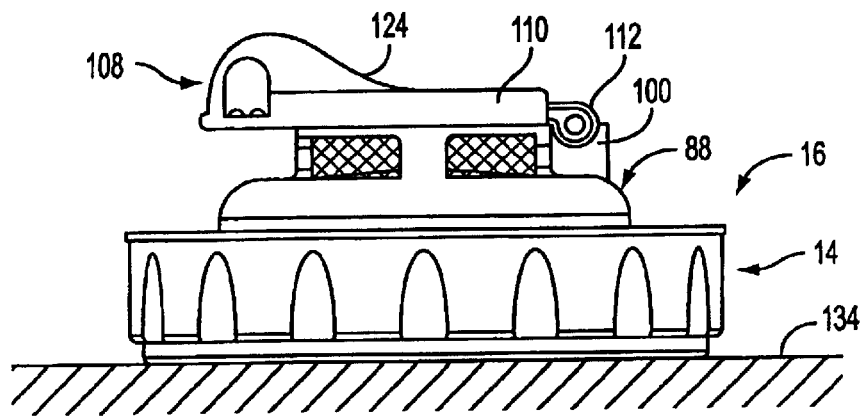
FIG. 7 is a side view of the sample holder of FIG. 6 showing the closure in a closed position.
Figure 8:
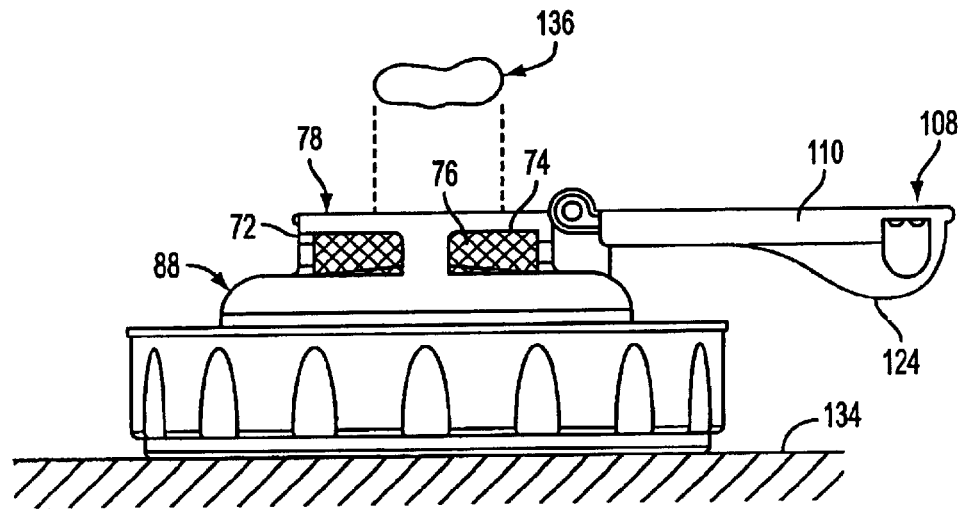
FIG. 8 is a side view of the sample holder of FIG. 6 showing the closure in an open position.
Figure 9:
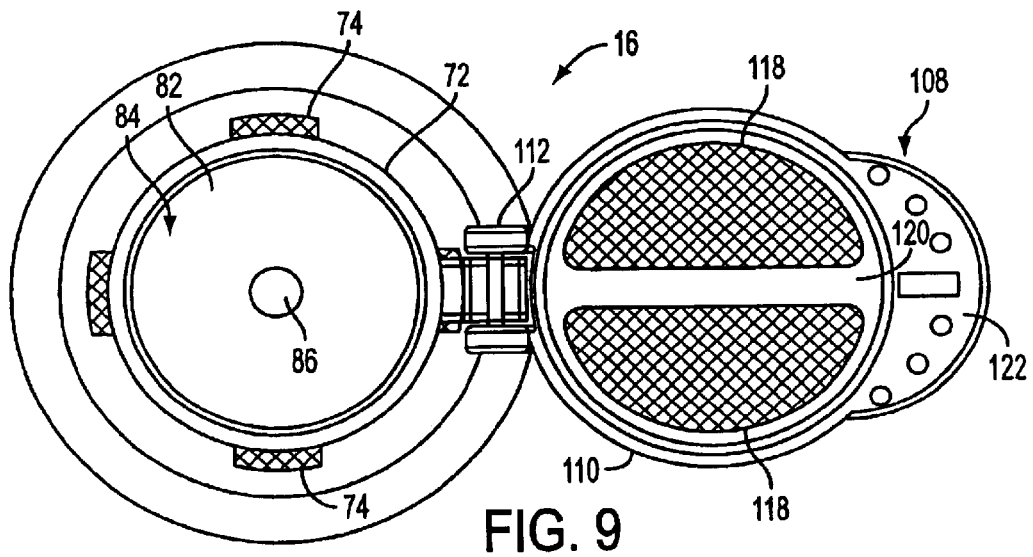
FIG. 9 is a top view of the sample holder of FIG. 8.

In use, cap 14 is removed from container 12, which is preferably prefilled with a liquid reagent. The permeable material covering the openings of sample holder 16 allow the liquid stabilizing agent to drain directly into container 12. Cap 14 is then inverted and placed on horizontal surface 134 as shown in FIG. 7. When inverted to the position shown in FIG. 7, bottom wall 82 of sample holder 16 allows any remaining liquid reagent to drain outwardly from cavity 84 through permeable material 76 covering openings 74 in side wall 72 where the reagent is collected in the inverted cap. Closure 108 is pivoted to the open position shown in FIG. 8 and a biological sample 136 is placed in cavity 84 of sample holder 16. Closure 108 is then pivoted to the closed position to contain biological sample 136 in cavity 84.

In preferred embodiments, closure cap 14 and sample holder 16 are coupled to container 12 in a manner to immerse biological sample 136 and cavity 84 completely in a liquid reagent 138. As shown in FIG. 10, cavity 84 of sample holder 16 is oriented to be positioned in a central area of container 12 spaced substantially equidistant between side walls 18 and between bottom wall 20 and cap 14. Cavity 84 is spaced from the bottom wall 20 and side wall 18 of container 12 and positioned below the level of liquid reagent 138. Preferably, container assembly 10 is prefilled with liquid reagent 138 with a volume sufficient to treat biological sample 136.

As shown in FIG. 10, base 88 of sample holder 16 has an outer dimension to define a volume sufficient to displace a portion of the air and the liquid in container 12 and to reduce the head space 140 above liquid reagent 130 when closure cap 14 is coupled to container 12. In a similar manner, body portion 54 of closure cap 14 has a volume to displace an amount of air and liquid reagent in container 12 and to reduce head space 140. Preferably, the liquid level is raised so that head space 140 is reduced to a sufficiently small volume so that cavity 84 and biological sample 136 are completely immersed in liquid reagent 138 regardless of the orientation of container assembly 10. Biological sample 136 is removed from container assembly by removing closure cap 14 and allowing the liquid reagent 138 to drain into container 12. Cap 14 is then placed on a horizontal surface with sample holder 16 facing upwardly. Any remaining liquid reagent can drain from cavity 84 into cap 14. Closure 108 is then opened so that biological sample 136 can be removed and processed as desired.

Container assembly 10 is particularly suitable for containing a stabilizing agent for preserving nucleic acid in a biological sample. To ensure adequate contact of biological sample 136 with the reagent, body 54 of sample holder 16 preferably includes permeable material 76 and 132 to allow continuous circulation of reagent 138 through cavity 84. The volume of reagent 138 necessary to effectively stabilize biological sample 136 can depend on the nature and concentration of the reagent. In preferred embodiments, the ratio of the volume of container 12 to the volume of cavity 84 can range from about 5:1 to about 12:1. Preferably, the ratio of the volume of reagent 138 in container 12 to the volume of cavity 84 containing biological sample 136 is at least about 5:1 and typically about 10:1. This ensures a suitable ratio of at least 10:1 of the volume of the reagent and the volume of the biological sample.

Cavity 84 of sample holder 16 has a dimension to contain an appropriate size and dimension of a biological sample in relation to the volume of the reagent in the container. In one embodiment, cavity 84 is about 2 cm in diameter and about 0.75 cm deep. Preferably, cavity 84 has a dimension to receive a sample ranging from 1 mm to about 5 cm in at least one dimension. For example, cavity 84 can have a dimension to receive a core needle biological sample having a length of about 3 cm and a diameter of about 1–2 mm. Cavity 84 can also be dimensioned to receive larger samples ranging from about 3.5 cm to about 5 mm. In preferred embodiments, porous material 76 and 132 have a sufficient small pore size to be able to strain small particles of the biological sample from the reagent and the container.

In one embodiment, the reagent is an aqueous medium containing one or more agents for stabilizing cells and biological samples. In one embodiment, the preserving and stabilizing agent is able to preserve nucleic acid in the biological sample for extended periods of time prior to nucleic acid analysis or isolation from the cells. The stabilizing agent included in the container is an amount effective to penetrate the cells and biological sample to prevent or inhibit nucleases from decomposing the nucleic acid.

The method of the invention contacts a biological sample with a treating reagent in a minimum predetermined ratio to ensure contact of the tissue sample with an effective or critical amount of the reagent sufficient to treat the sample for the intended purpose. The volume of the biological sample is controlled in relation to the amount of the reagent to regulate the ratio of the relative amount of the biological sample to the amount of the reagent. In preferred embodiments of the invention, the ratio of the relative volume of the reagent to the biological sample is at least 5:1. Typically, the ratio of the volume of reagent to the volume of the biological sample is at least about 10:1. The critical amount of the reagent to treat a biological sample effectively can vary depending on the particular sample and the particular reagent. The amount of reagent required to treat a sample effectively is affected by the weight, volume and density of the sample. For example, some tissue samples are dense compared to other tissues and may require more or less of a particular reagent than that required by a less dense or porous tissue.

The biological samples that are treated by the methods of the invention are typically tissue samples. Examples of biological samples that can be treated include organ specimens, tumor specimens, bone specimens, and connective tissue specimens, such as tendons and membranes.

The reagent for treating the biological sample is preferably a liquid but can be a gel or viscous material. The treating reagent is typically an aqueous or alcohol solution containing a suitable reagent, such as a stabilizing agent or fixative reagent. Examples of suitable reagents include stabilizing agents, lysing agents, drying agents, preservation reagents, and cationic detergents. The reagents can be organic or inorganic compounds. In one embodiment, the reagent is a 10% by volume aqueous formaline solution.

The method and apparatus of the invention are particularly suitable for use in transporting a biological sample to another location, such as to a remote laboratory, while stabilizing and preserving the sample. The method of the invention in one embodiment collects a biological sample, such as a tissue sample, and immediately places the sample in the container assembly to immerse the sample in the reagent contained within the container assembly. The container assembly is able to retain the biological sample immersed in the reagent while being transported and to provide an amount of the reagent sufficient to treat the sample. In one embodiment, the reagent is a nucleic acid stabilizing reagent that is able to preserve the nucleic acids in the cells of the sample for extended periods of time. Preferably, the sample is collected and immediately immersed in the stabilizing reagent to enable high quality quantitative and qualitative analysis of the nucleic acids.

The reagent is typically an aqueous medium or alcohol containing one or more components for treating the biological sample. In one embodiment, the reagent is for stabilizing cells and biological samples. In one preferred embodiment, the preserving and stabilizing reagent is able to preserve nucleic acids for extended periods of time prior to isolation from the cells. The stabilizing reagent included in the container is an amount effective to penetrate the cells and biological sample to prevent or inhibit nucleases from decomposing the nucleic acids.

In another embodiment, the stabilizing agent is able to precipitate nucleic acid and the cellular protein in the sample to inhibit or inactivate the action of the nuclease. In this embodiment, the stabilizing agent is an aqueous medium containing a salt that is able to precipitate the nucleic acid and cellular proteins. Examples of suitable salts are sulfates, such as ammonium sulfate, ammonium bisulfate, cesium sulfate, cadmium sulfate, cesium iron (II) sulfate, chromium (III) sulfate, cobalt (II) sulfate, copper (II) sulfate, lithium sulfate, magnesium sulfate, manganese sulfate, potassium sulfate, sodium sulfate and zinc sulfate. The salt concentration can range from about 0.10 to 1.50 g/ml, and preferably about 0.7 g/ml. In other embodiments, the stabilizing agent can include formalin or a chaotropic salt such as quanidium compounds. The stabilizing agent can also include amounts of ethanol, methanol, acetone, trichloracetic acid, propanol, polyethylene glycol, acetic acid and a chelating agent such as EDTA. Buffering agents such as sodium acetate can also be added. Generally, the stabilizing agent has a pH of about 4–8.

The reagents are generally liquids that can pass through the porous mesh of the sample holder to contact the biological sample. In other embodiments, the reagent can be a gel, solid or semi-solid in the form of beads or particles. The gel and the beads can be permeable or impermeable to the porous mesh of the sample holder. Typically the beads or particles of the reagent have a particle size that is larger than the opening size of the mesh of the sample holder and are not permeable to the mesh. In embodiments where the gel or beads are impermeable to the mesh of the sample holder, the cavity of the sample holder can contain an amount of the gel, beads or particles to contact the biological sample. The dimensions of the cavity are selected to provide the necessary volume ratio of the biological sample to the reagent. The gel can be permeable to the permeable mesh of the sample holder to pass through the walls of the sample to contact and immerse the biological sample in the reagent. The solid or semi-solid reagent, such as beads or particles, can be used alone although they are typically used in combination with a liquid or gel reagent to supplement the solid or semi-solid reagent so the biological sample is maintained immersed in the reagents. In this embodiment, the cavity of the sample holder can contain the solid or semi-solid reagent and the container can contain the liquid or gel reagent that is permeable to the wall of the sample container. In this manner the biological sample is placed in the sample holder in contact with the solid or semi-solid reagent. The sample holder is then placed in the container with the liquid or gel reagent to enable the reagent to flow through the walls of the sample holder to contact fill the spaces between the beads or particles and to completely surround the biological sample with a reagent.

Figure 11:
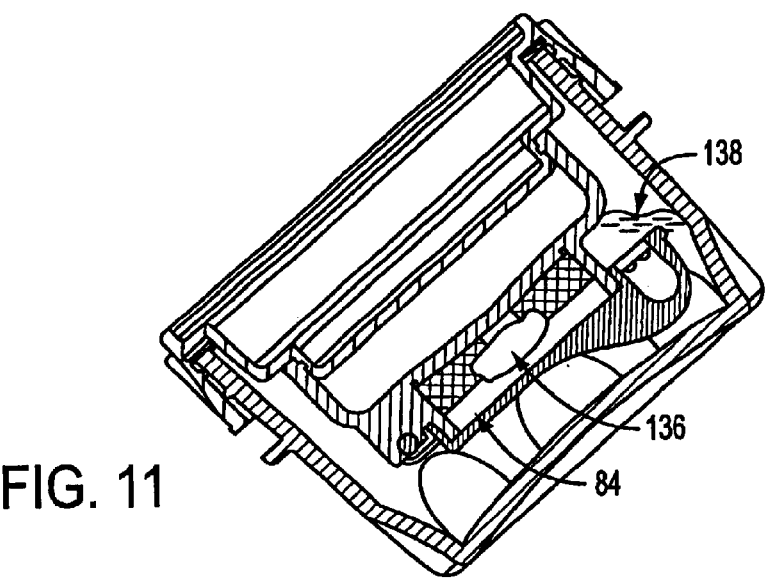
FIG. 11 is a cross-sectional side view of the sample holder oriented at about 45° and showing the cavity of the sample holder immersed in the reagent.
Figure 12:
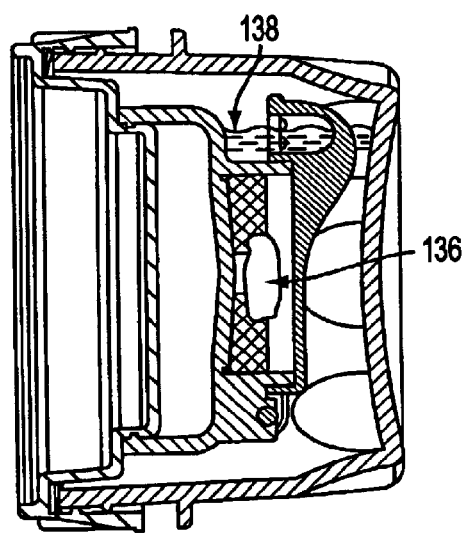
FIG. 12 is a cross-sectional side view of the sample holder oriented on its side and showing the cavity of the sample holder immersed in the reagent.

Container assembly 10 is constructed to define an internal containment area within container 12 to retain biological sample 136 in a predetermined area of container 12. Preferably, a containment area is defined by cavity 84 of sample holder 16. As shown in FIGS. 10–12, the containment area defined by cavity 84 is oriented in substantially the center of container 12 between the sides of container 12, cap 14, and bottom wall 20. As shown, reagent 138 is filled to a level to completely immerse cavity 84. Cavity 84 and reagent 138 are selected and controlled to maintain cavity 84 completely immersed in reagent 138 without regard to the orientation of container 12 as shown in FIGS. 11 and 12. In this manner, the biological sample will remain completely immersed in the reagent during handling and transporting of the container. Containing the biological sample in an area that is consistently below the level of the treating reagent regardless of the orientation of the container substantially prevents the biological sample from contacting the air in the container. Retaining the biological sample completely immersed in the treating reagent enhances complete treatment of the sample with the reagent and minimizes inaccuracies in the test results that can occur when the sample is exposed to air even for short periods of time. Certain reagents, such as nucleic acid stabilizing reagents, are most effective when the sample is immediately immersed in the reagent. Exposing the biological sample to air can lower the accuracy of the nucleic acid analysis.

In the embodiment of FIGS. 1–10, a sample holder having a cavity for receiving a biological sample is coupled to cap 14 and fits within a container 12 that contains a liquid reagent. The closure cap closes the open top end of the cavity of the sample holder and closes the container in a manner to retain the biological sample completely immersed in the reagent. In preferred embodiments, the body 108 of sample holder 16 and cap 14 displace a sufficient amount of air from the head space and displaces a portion of the reagent in the container to raise the level of the reagent above the cavity of the sample holder. In addition, displacing air in the head space above the reagent ensures that the biological sample is completely submerged in the reagent at all times. Preferably, the container contains a sufficient amount of the reagent so that the biological sample remains immersed regardless of the orientation of the container assembly. The cavity of the sample holder defines a containment area within the container to retain the biological sample below the surface of the reagent.

Container assembly 10 is preferably made of a suitable plastic material that is non-reactive with the stabilizing agents and does not interfere with the biological sample. The components of container assembly 10 are generally made by a suitable injection molding process as known in the art.

In one embodiment of the invention, container assembly 10 is prefilled with a liquid reagent 104, such as a nucleic acid stabilizing reagent. Container assembly 10 is sealed, packaged and shipped to the technician or physician for receiving and storing a biological sample. Container assembly 10 can include a suitable seal or tamper indicator. In other embodiments, container assembly 10 can be packaged without a reagent and shipped to the consumer empty. Cap 14 is removed and container 12 is filled with a suitable reagent at the time of use.

Container assembly 10 is primarily intended for use with liquid reagents that can permeate through the porous material of the sample holder. Typically, it is desirable to provide an amount of the reagent in a suitable ratio by volume of the reagent to the biological sample and where the liquid reagent flows through the porous material to replenish the reagent in the cavity of the sample holder. In alternative embodiments, the reagent can be a gel or gel-like material that can permeate the porous material of the sample holder. In other embodiments, the porous material is not permeable to the gel or gel-like reagent. Where the porous material of the sample holder is not permeable to the gel or gel-like reagent, the cavity of the sample holder can contain an effective amount of the reagent to treat the biological sample. In still other embodiments, the reagent can be in the form of particles or beads that are able to effectively treat the biological sample.

Embodiment of FIGS. 13–16

Referring to FIGS. 13–16, a second embodiment of the invention is illustrated. In this embodiment, a closure cap 150 and sample holder 152 cooperate with a container 153 for containing a reagent for treating the biological sample. In other embodiments, the container 153 can be similar to container 12 of the embodiment of FIGS. 1–10.

Figure 13:
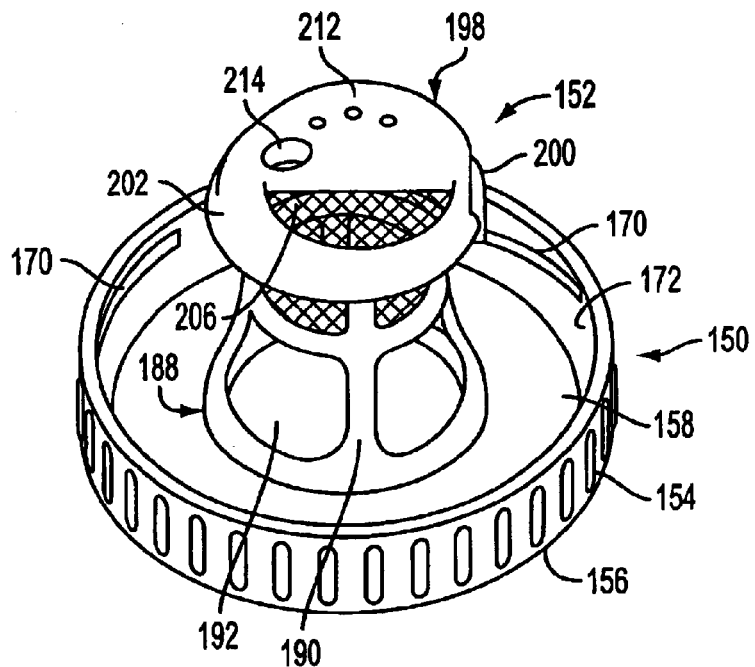
FIG. 13 is a perspective view of the sample holder and cap in a second embodiment.

Referring to FIG. 13, cap 150 includes a side wall 154 having a top end 156 connected to a top wall 158. Top wall 158 is formed with an annular rib 160. Rib 160 is defined by an outer annular wall 162, an inner annular wall 164 and a connecting wall 166. Rib 160 defines a substantially circular recess 168. As in the previous embodiment, side wall 154 includes threads 170 on an inner face for coupling with a container.

Sample holder 152 has a generally basket-like structure with an annular side wall 174 having a plurality of openings 176. A liquid permeable material 178 is applied to side wall 174 to cover openings 176 to allow liquid to pass through while retaining a biological sample within sample holder 152. Side wall 174 has an inner surface 180 with a rib 182 extending radially inward. Rib 182 extends inwardly to define an opening 184. Opening 184 is covered by a porous material 186. Rib 182 and porous material 186 define an internal cavity 194 of sample holder 152 with an open top end 196.

Sample holder 152 includes a base 188 having an annular shape complementing the dimensions of recess 168 in cap 14. Base 188 is connected to side wall 174 of sample holder 152 by a plurality of legs 190. Legs 190 are spaced apart to define openings 192 between adjacent legs 190 to allow the flow of the reagent around sample holder 152. In a preferred embodiment, base 188 is coupled to cap 150 by press fitting base 188 into recess 168.

Figure 14:
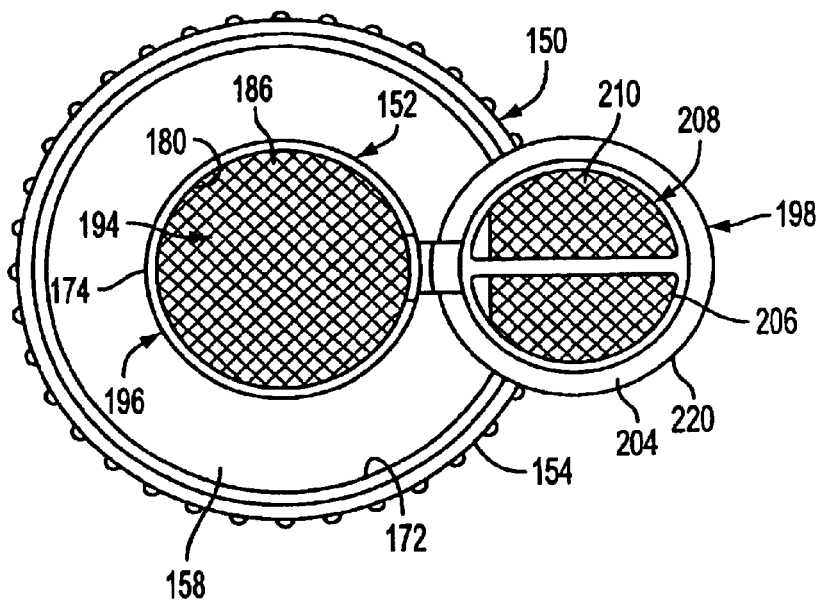
FIG. 14 is a top view of the sample holder of FIG. 11.
Figure 15:
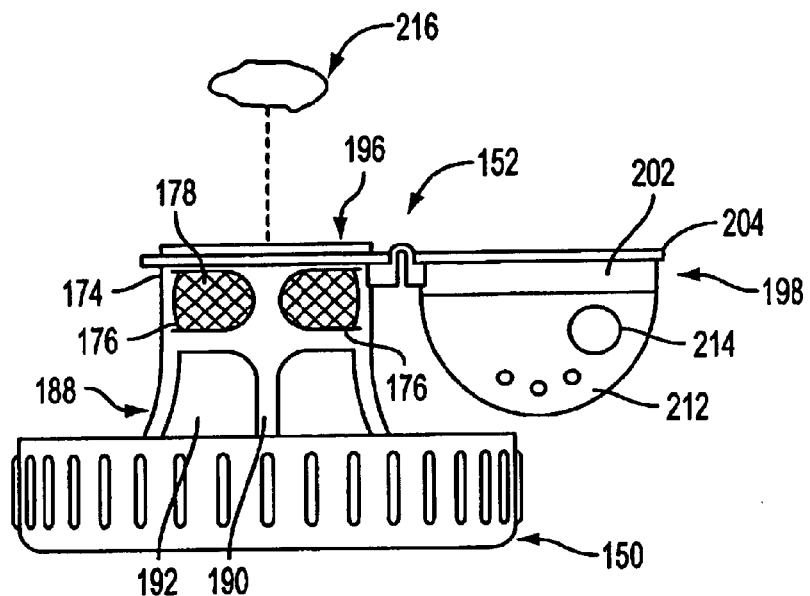
FIG. 15 is a side view of the sample holder of FIG. 13 and the container.

A closure 198 is coupled to a top end of side wall 174 by a hinge 200 so that closure 198 can pivot between an open position shown in FIGS. 14 and 15 and a closed position shown in FIG. 13. Closure 198 has a side wall 202 with an outwardly extending collar 204 at a bottom end and an inwardly extending collar 206 at a top end. Inwardly extending collar 206 defines an opening 208. Preferably, opening 208 is covered by a permeable material 210 to allow liquid to flow freely into cavity 194. A handle 212 extends upwardly from side wall 202 for manipulating closure 198. In the embodiment illustrated, handle 212 includes an aperture 214 to assist in opening and closing closure 198.

Side wall 202 of closure 198 has an inner dimension complementing the outer dimension of side wall 174 of sample holder 152. Preferably, side wall 202 of closure 198 and side wall 174 of sample holder 152 include cooperating detents for retaining closure 198 in a closed position.

Figure 16:
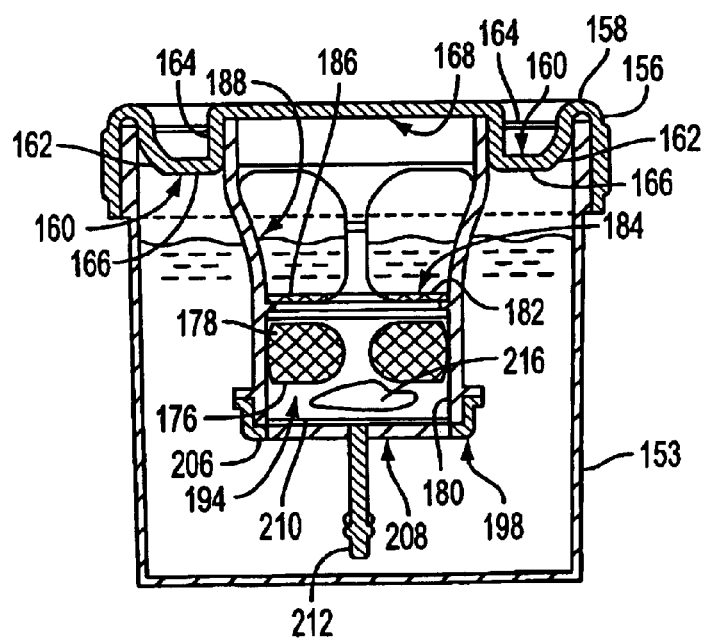
FIG. 16 is a cross-sectional side view of the container assembly including the sample holder of FIG. 13.

In use, closure cap 150 is separated from the respective container and lifted upwardly allowing the liquid reagent to drain back into the container 153. Cap 150 is then placed on a horizontal surface with sample holder 152 facing upwardly. Any remaining liquid reagent retained in cavity 194 drains downwardly and is collected in cap 150. Closure 198 is opened and a biological sample 216 is placed in cavity 194. Closure 198 is then pivoted to the closed position and cap 150 is coupled to the container 153 so that cavity 194 and biological sample 216 are completely immersed in the liquid reagent as shown in FIG. 16. In preferred embodiments, legs 190 that connect base 188 to side wall 174 have a length to space cavity 194 a sufficient distance from cap 150 to ensure that biological sample 216 remains immersed in the liquid reagent regardless of the orientation of the container assembly.

Embodiment of FIGS. 17–20

Figure 17:
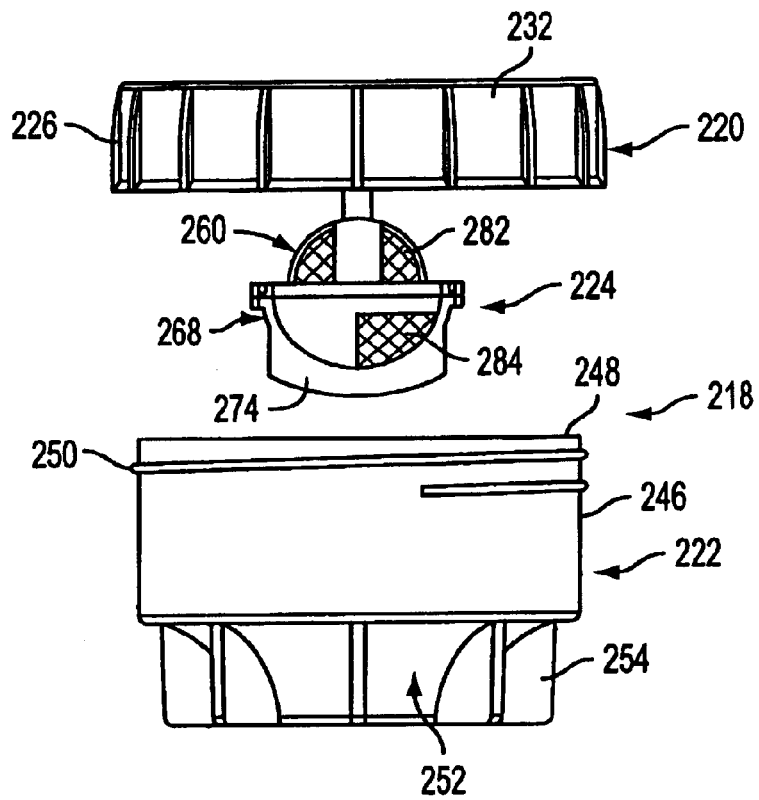
FIG. 17 is an exploded side view of the container assembly in another embodiment of the invention.

Referring to FIGS. 17–20, another embodiment of the invention is illustrated for storing a biological sample in a reagent. Referring to FIG. 17, a container assembly 218 includes a closure cap 220, container 222, and a sample holder 224.

Closure cap 220 includes a side wall 226 having an inner surface 228 with threads 230 for coupling with container 222. Side wall 226 has an outer surface 232 with ribs 234 for gripping cap 220.

Figure 20:
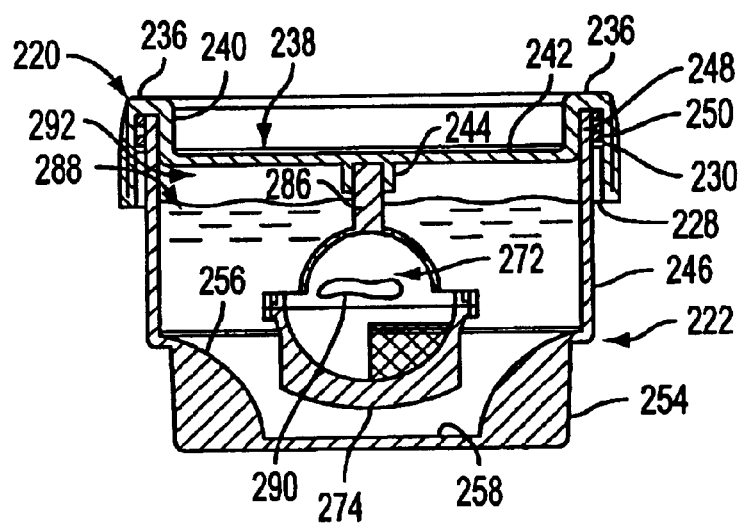
FIG. 20 is a cross-sectional side view of the sample holder and lid on the container.

As shown in FIG. 20, cap 220 has a top wall 236 and a body portion 238 extending axially inward from top wall 236. Body portion 238 has an annular side wall 240 spaced inwardly from side wall 226 and an end wall 242 spaced from top wall 236. An annular collar 244 extends axially from an inner surface of end wall 242 for coupling with sample holder 224.

Container 222 has a cylindrical side wall 246. Side wall 246 has a top end 248 with external threads 250 for mating with threads 230 of cap 220. Container 222 is formed with a bottom portion 252 with outwardly extending ribs 254 for manipulating container 222. Bottom portion 252 has a generally convex side wall 256 and a bottom wall 258.

Sample holder 224 in the embodiment illustrated has a basket-like structure and has a substantially spherical shape. Sample holder 224 has a bottom section 260 having a generally semi-spherical shaped side wall 262 with an open top end 264. A flange 266 extends radially outward from the open top end 264 of side wall 262.

Sample holder 224 also includes a top section 268 that is pivotally connected to bottom section 260 by a hinge 270. Top section 268 has a semi-spherical shape complementing bottom section 260 for defining an internal cavity 272 when top section 268 is in the closed position shown in FIG. 20. Top section 268 includes a handle 274 extending upwardly from side wall 276.

Side wall 262 and side wall 276 are preferably formed with openings 278 and 280, respectively. Openings 278 and 280 are covered by a porous material 282 and 284, respectively. Bottom section 260 includes a base 286 extending from side wall 262 opposite open top end 264. Base 286 in the embodiment illustrated, is a cylindrical post having a dimension complementing collar 244 for coupling sample holder 224 to cap 220 as shown in FIG. 20. Preferably, base 286 has an axial length sufficient to position sample holder 224 within container 222 so that cavity 272 is completely immersed in a reagent 288 regardless of the orientation of container 222.

Figure 18:
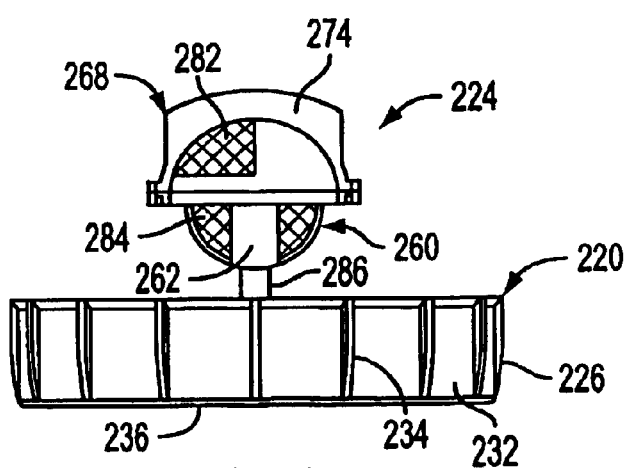
FIG. 18 is a side view of the sample holder of the embodiment of FIG. 17 with the closure in the closed position.
Figure 19:
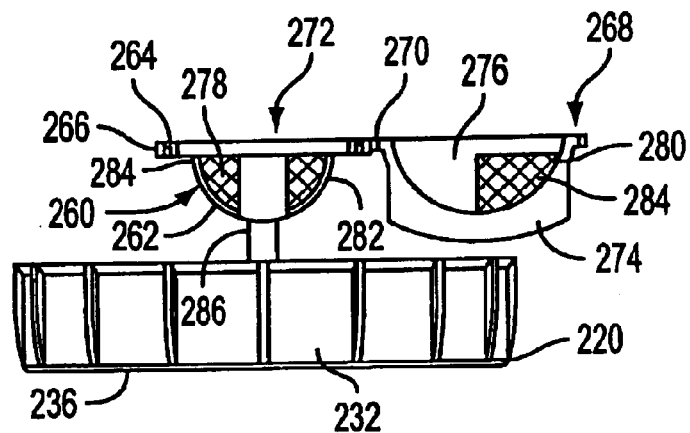
FIG. 19 is a side view of the sample holder of the embodiment of FIG. 18 in the open position.

Container assembly 218 is used in a similar manner as in the previous embodiments. Basically, cap 220 is removed from container 222 and the liquid reagent 288 is allowed to drain into container 222. Cap 220 is placed on a horizontal surface with sample holder 224 facing upwardly as shown in FIG. 18. Any remaining liquid in cavity 272 is allowed to drain downwardly and collected in cap 220. A biological sample 290 is placed in cavity 272 and top section 268 is pivoted to the closed position to retain biological sample 290 within cavity 272. Cap 220 and sample holder 224 are then replaced on container 222 to immerse sample holder 224 and biological sample 290 in liquid reagent 288. As shown in FIG. 20, body portion 238 of cap 220 has a dimension to displace a portion of the air in container 222 to minimize the head space 292 above liquid reagent 288.

Figure 21:
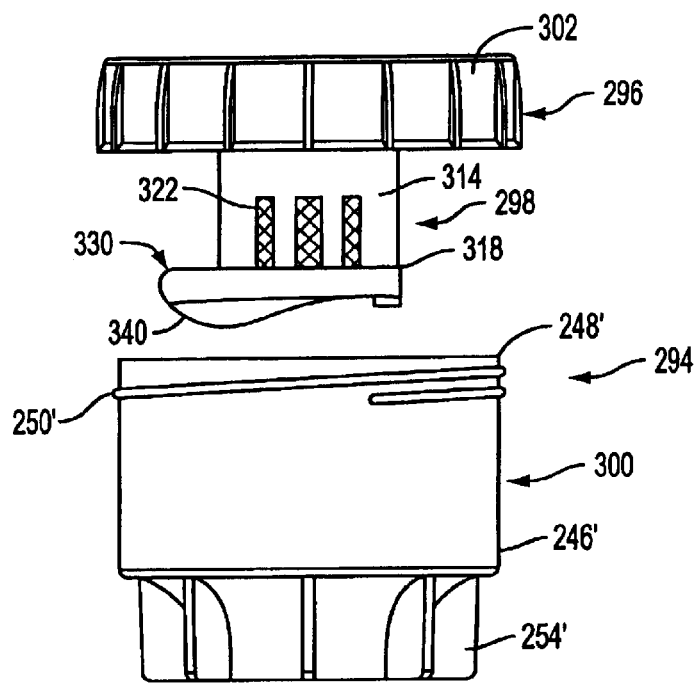
FIG. 21 is an exploded side view of the sample holder in another embodiment.
Figure 22:
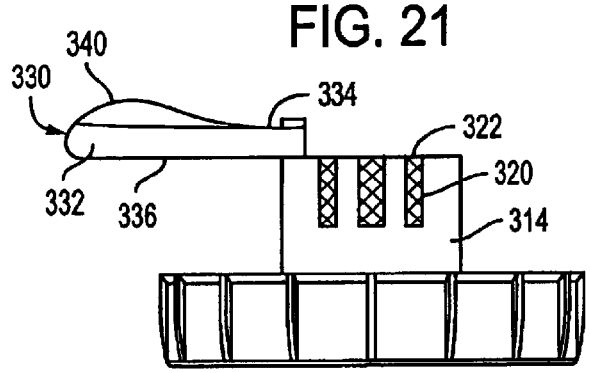
FIG. 22 is a side view of the sample holder showing the closure in the open position.
Figure 23:
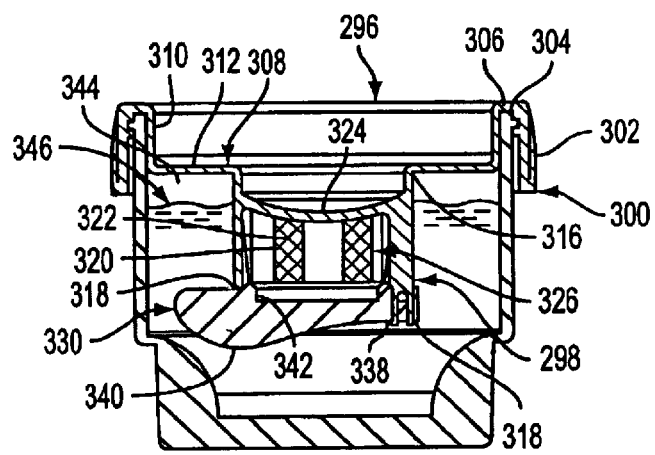
FIG. 23 is a side view of the container assembly in cross-section.

Embodiment of FIGS. 21–23

Referring to FIGS. 21–23, another embodiment of the invention is illustrated. The container assembly 294 includes a closure cap 296, a sample holder 298 and a container 300. Container 300 is substantially the same as the embodiment of FIGS. 17–20 so that identical components are identified by the same reference number with the addition of a prime.

Cap 296 includes a side wall 302 having internal threads 304 and a top wall 306. A body portion 308 extends axially from top wall 306 toward a bottom end of side wall 302. As shown in FIG. 23, body 308 is formed by an annular side wall 310 and an end wall 312. Side wall 310 extends substantially parallel to side wall 302 in the illustrated embodiment.

In the embodiment illustrated, sample holder 298 is integrally formed with cap 296. Typically, cap 296 and sample holder 298 are molded from a plastic material as a single unit. Sample holder 298 includes an annular side wall 314 having a bottom end 316 coupled to body 308 and an outer end 318. As shown in FIG. 21, side wall 314 includes a plurality of openings 320 covered by a porous material 322. Openings 320 in side wall 314 extend from bottom wall 324 toward outer end 318 of side wall 314.

Sample holder 298 also includes a bottom wall 324 coupled to side wall 314. As shown in FIG. 23, bottom wall 324 has a substantially convex surface facing an internal cavity 326. Side wall 314 is provided with a post 328 extending axially from outer end 318.

A closure member 330 is pivotally coupled to post 328 and is pivotable about an axis parallel to side wall 314. Closure 330 in the embodiment illustrated has a planar body 332 with a top face 334 and a bottom face 336. Body 332 includes an aperture 338 for cooperating with post 328 to enable closure 330 to pivot about an axis that is parallel to a longitudinal axis of cavity 326. A handle 340 is provided on top face 334 of body 332 for manipulating closure 330. Bottom face 336 of body 332 is provided with an annular rib 342 for mating with side wall 314 for securing closure 330 in a closed position as shown in FIG. 23.

In the embodiment illustrated, body 332 of closure 330 is substantially solid. In alternative embodiments, body 332 can include openings covered by a suitable porous material to allow the flow of a liquid reagent into cavity 326.

The use of container assembly 294 is similar to the previous embodiments. Preferably, container assembly 294 is prefilled with a liquid reagent at the time of manufacture. Cap 296 and sample holder 298 are removed from container 300 so that the liquid reagent drains into container 300. Cap 296 is placed on a horizontal surface with sample holder 298 facing upwardly. Any remaining liquid reagent in cavity 326 is directed toward side wall 314 by the convex bottom wall 324 so that the liquid drains through porous material 322 and is collected in cap 296. Closure 330 is opened and a biological sample is placed in cavity 296. Closure 330 is then closed and cap 296 and sample holder 298 secured to container 300. In preferred embodiments, body 308 of cap 296 has a dimension to displace a portion of the air and liquid reagent in container 300 to reduce the head space 344 above liquid reagent 346. By reducing the head space 344 and air in container 300, the biological sample remains completely immersed in the liquid reagent regardless of the orientation of container assembly 294.

Figure 24:
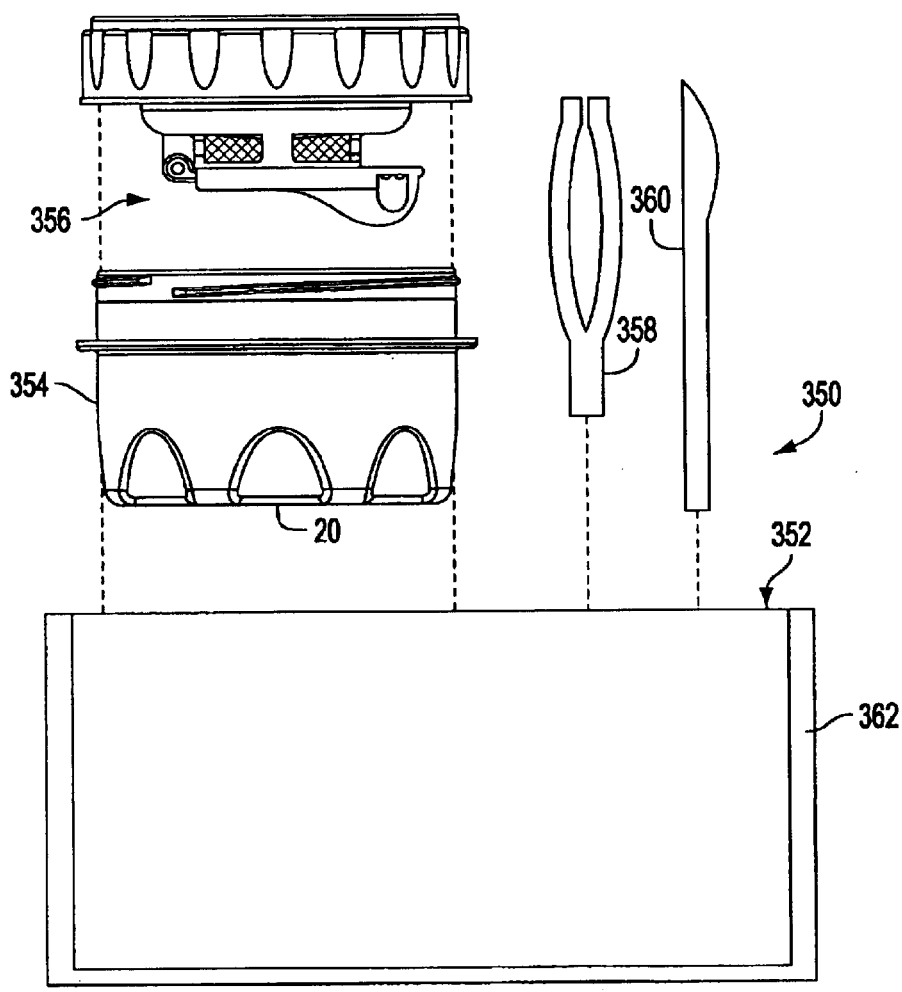
FIG. 24 is an exploded side view of the kit showing the package, container and surgical tools.
Figure 25:
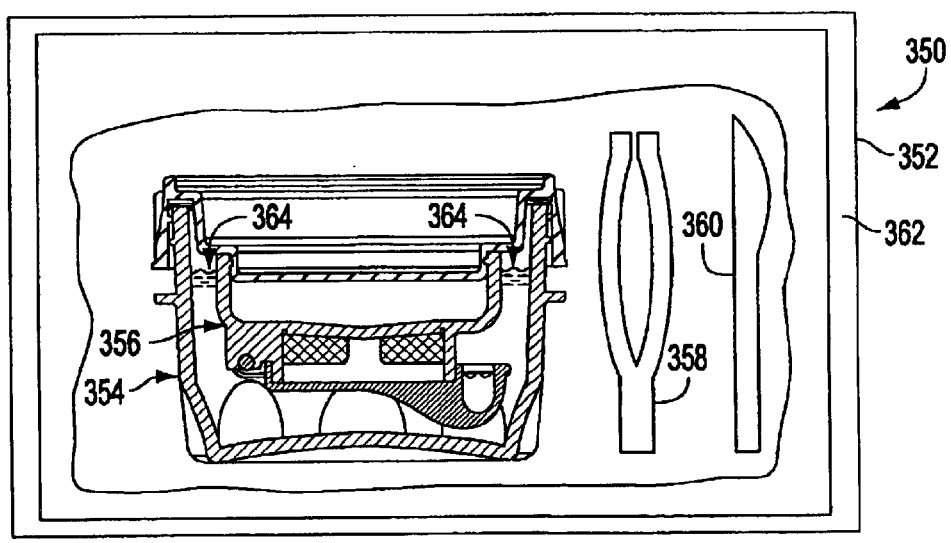
FIG. 25 is a side view in partial cross-section of the kit of FIG. 24.

Embodiment of FIGS. 24–25

FIGS. 24 and 25 show an embodiment of the invention in the form of a prepackaged sterile kit 350 for use by the physician or clinician. The kit 350 includes a package 352 enclosing a container 354, a sample holder 356 and one or more tools, such as a pair of forceps 358 and a scalpel 360. Preferably, the tools are clean and sterile to be ready for use. Package 352 in the illustrated embodiment is a plastic pouch formed a sheet of plastic film or material that can be heat sealed around one or more of the edges 362. The heat sealed edges 362 can be formed as peel layers that can be readily separated by the operator to remove the contents.

In one embodiment shown in FIG. 25, container 354 is prefilled with a liquid reagent 364 and sample holder 356 packaged within container 354. Alternatively, sample holder 356 is packaged separate from container 354. In the embodiment illustrated, a pair of forceps 358 and a scalpel 360 are included in package 352, although other tools and surgical tools such as a measuring gauge can be included. The tools can also be enclosed within a separate pouch within the package 252.

While various embodiments have been chosen to illustrate the invention, it will be understood by those skilled in the art that various modifications and additions can be made without departing from the scope of the invention as defined in the appended claims.

What is claimed is:

1. A container assembly for storing a biological sample, said assembly comprising:

a container having a bottom, a side and an open top end, said container having a dimension to contain a volume of a reagent sufficient to treat a biological sample;

a closure cap for coupling to said open top end of said container; and a sample holder coupled to said cap and being positioned to be received in said container, said sample holder having an internal cavity with a dimension for receiving a biological sample, said sample holder having a plurality of fluid openings into said cavity to enable free flow of said reagent into said cavity while retaining said biological sample in said cavity, said sample holder having a dimension to fit between said bottom and side of said container and said cap and to immerse said cavity in said reagent, said sample holder including a base member having a width equal to or greater than a width of said internal cavity to displace a predetermined portion of said reagent in said container and to reduce a head space above said reagent in said container and to maintain said internal cavity of said sample holder immersed in said reagent, said cavity of said sample holder having a volume to limit the size of said biological sample to maintain a predetermined ratio of an amount of said biological sample to an amount of said reagent to treat said biological sample.

2. The container assembly of claim 1, wherein said sample holder has a bottom wall and a side wall defining said cavity, said bottom wall including a permeable member defining said fluid openings.

3. The container assembly of claim 2, wherein said side wall includes a permeable member to allow free flow of said reagent into said sample holder.

4. The container assembly of claim 1, wherein said sample holder includes a bottom, a side wall, an open end and a closure member for closing said open end.

5. The container assembly of claim 4, wherein said closure member is coupled to said sample holder and is pivotable about an axis oriented in a plane parallel to a plane of said side wall.

6. The container assembly of claim 4, wherein said closure member includes a porous material to enable the flow of said reagent into said sample holder.

7. The container assembly of claim 4, wherein said closure member is coupled to said sample holder and pivotable about an axis oriented in a plane perpendicular to a plane of said side wall.

8. The container assembly of claim 4, wherein said side wall and said bottom include a porous material to enable said treating liquid to flow into said sample holder.

9. The container assembly of claim 4, wherein said sample holder includes a base, and wherein said base is coupled to said cap for spacing said sample holder from said cap and immersing said sample holder in said reagent.

10. The container assembly of claim 9, wherein said base comprises an annular wall having an axial dimension and width defining a volume to displace a portion of air and said reagent in said container to immerse said cavity of said sample holder in said reagent.

11. A container assembly for storing a biological sample, said assembly comprising:

a container having a bottom, a side and an open top end, said container having a dimension to contain a volume of a reagent sufficient to treat a biological sample;

a closure cap for coupling to said open top end of said container; and a sample holder coupled to said cap and being positioned to be received in said container, said sample holder having an internal cavity with a dimension for receiving a biological sample, said sample holder having a plurality of fluid openings into said cavity to enable free flow of said reagent into said cavity while retaining said biological sample in said cavity, said sample holder having a dimension to fit between said bottom and side of said container and said cap and to immerse said cavity in said reagent, said cavity of said sample holder having a volume to limit the size of said biological sample, said container having an internal volume and said sample holder having an internal volume, and wherein the ratio of said internal volume of said container and said internal volume of said sample holder is at least 5:1.

12. The container assembly of claim 4, wherein said closure member of said sample holder includes a top face and a handle member extending from said top face.

13. The container assembly of claim 1, wherein said cap has an axial dimension including a top wall lying in a plane, said top wall having a body portion extending outwardly from said top wall, said body portion having a dimension sufficient to displace a volume of air from said container and to reduce a head space above said reagent.

14. The container assembly of claim 13, wherein said body portion of said top wall includes an annular side wall extending in an axial direction with respect to said top wall and having an end wall coupled to an outer end of said side wall, and wherein said sample holder includes a base member having an annular wall coupled to said side wall of said body portion.

15. The container assembly of claim 14, wherein said base member of said sample holder has a dimension to displace a portion of said reagent from said container.

16. The container assembly of claim 1, further comprising a closure member pivotally coupled to said side wall of said sample holder to close said open end, and wherein said side wall and closure include at least one porous portion.

17. The container assembly of claim 1, wherein said container contains a reagent in an amount sufficient to treat a biological sample, and wherein said reagent is included in an amount to provide a ratio of a volume of said reagent to a volume of a biological sample of at least 10:1.

18. A container assembly, comprising:

a container having a bottom, a side and an open top end, and being dimensioned to contain a biological sample treating reagent in a volume sufficient to treat a biological sample;

a closure cap removably coupled to said container and closing said open top end, said closure cap having an outer face and an inner face;

a sample holder coupled to said inner face of said cap, said sample holder having a side wall with at least one open area, and an internal cavity for receiving a biological sample, and at least one fluid opening into said cavity, said sample holder having a dimension to fit within said container to completely immerse said cavity in said reagent, said sample holder being positioned with respect to said inner face of said cap to substantially prevent linear movement of said sample holder in said container; and a body integrally formed with said sample holder and extending from said inner face of said closure cap and having a dimension to displace a portion of said air and reagent in said container to completely immerse said sample holder in said reagent and where said side wall of said sample holder extends axially from said body.

19. The container assembly of claim 18, wherein said body is integrally formed with said cap and extends from said inner face in a substantially axial direction with respect to a center axis of said cap.

20. The container assembly of claim 18, wherein said body is coupled to said cap.

21. The container assembly of claim 20, wherein said sample holder includes a porous member closing said at least one open area.

22. The container assembly of claim 21, wherein said side wall of said sample holder includes an open end, and a closure member for closing said open end.

23. The container assembly of claim 22, wherein said closure member of said sample holder includes at least one open area and a porous member closing said open area.

24. The container assembly of claim 18, wherein said body is integrally formed with said cap.

25. The container assembly of claim 24, wherein said sample holder has a base with a dimension to displace air from said container and reduce a head space above said reagent.

26. The container assembly of claim 18, wherein said sample holder includes a post having an outer end coupled to said cap, whereby said sample holder is spaced from said cap.

27. A container assembly for storing a biological sample, said assembly comprising:

a container having a bottom, a side and an open top end, said container having a dimension to contain a volume of a reagent sufficient to treat a biological sample;

a closure cap for coupling to said open top end of said container; and a sample holder coupled to said cap and being positioned to be received in said container, said sample holder having an internal cavity with a dimension for receiving a biological sample, and having a plurality of fluid openings into said cavity to enable free flow of said reagent into said cavity while retaining said biological sample in said cavity, said sample holder having a dimension to fit between said bottom and side of said container and said cap and to immerse said cavity in said reagent, said sample holder further having an annular side wall, a bottom, an open top and an annular base coupled to said closure cap and having an axial length to space said internal cavity from said closure cap.

28. The container assembly of claim 27, wherein said closure cap has a bottom side with a recess and where said base of said sample holder is received in said recess.

29. The container assembly of claim 27, wherein said sample holder has a plurality of legs extending between said annular base and said annular side wall.

30. The container assembly of claim 11, wherein said sample holder includes a post having a distal end coupled to said cap whereby said sample holder is spaced from said cap.

31. The container assembly of claim 30, wherein said sample holder comprises a first member and a second member pivotally coupled together and defining a substantially spherical shape, and wherein said first member and said second member include at least one liquid permeable section.

32. The container assembly of claim 31, wherein said sample holder further includes a base member extending from said first member, said base member having an outer end coupled to said cap for spacing said sample holder from said cap.

33. The container assembly of claim 11, wherein said sample holder has a bottom, a side wall, an open end and closure member closing said open end and having an outer face with a handle member extending from said outer face.

34. The container assembly of claim 11, wherein said closure cap has a bottom surface with a recess therein, and where said sample holder has a base received in said recess.

35. The container assembly of claim 34, wherein said base is defined by an annular wall.

36. The container assembly of claim 35, wherein said annular wall of said base has a plurality of openings defining legs extending from said sample holder.

37. The container assembly of claim 11, wherein said closure cap has a body portion with an annular outer surface and extending in an axial direction, and where said sample holder has a base with an annular wall coupled to said annular outer surface of said body.

38. The container assembly of claim 18, wherein said body is defined by an annular wall, and where said annular wall is coupled to said closure cap.

39. The container assembly of claim 38, wherein said annular wall of said body defines a hollow cavity to displace said reagent and air in said headspace of said container.

40. The container assembly of claim 39, wherein said body is integrally formed with said closure cap.

41. The container assembly of claim 39, wherein said closure cap has an inner surface and where said body is coupled to said inner surface of said closure cap.

42. The container assembly of claim 41, wherein said inner surface of said closure cap includes an annular wall and where said annular wall of said body mates with said annular wall of said closure cap.

* * * * *